(12) United States Patent
Souvie et al.

(10) Patent No.: US 7,994,359 B2
(45) Date of Patent: Aug. 9, 2011

(54) PROCESS FOR THE SYNTHESIS OF (7-METHOXY-1-NAPHTHYL) ACETONITRILE AND ITS APPLICATION IN THE SYNTHESIS OF AGOMELATINE

(75) Inventors: Jean-Claude Souvie, Le Havre (FR); Isaac Gonzalez Blanco, Toledo (FR)

(73) Assignee: Les Laboratoires Servier, Suresnes Cedex (FR)

( * ) Notice: Subject to any disclaimer, the term of this patent is extended or adjusted under 35 U.S.C. 154(b) by 284 days.

(21) Appl. No.: 12/313,921

(22) Filed: Nov. 26, 2008

(65) Prior Publication Data
US 2009/0118544 A1    May 7, 2009

Related U.S. Application Data

(62) Division of application No. 11/051,868, filed on Feb. 4, 2005, now Pat. No. 7,470,806.

(30) Foreign Application Priority Data

Feb. 13, 2004  (FR) ..................... 04 01437

(51) Int. Cl.
*C07C 253/14*   (2006.01)
(52) U.S. Cl. ........................................ 558/351
(58) Field of Classification Search ............ 558/351
See application file for complete search history.

(56) References Cited

U.S. PATENT DOCUMENTS
| | | | |
|---|---|---|---|
| 3,931,188 A | 1/1976 | Douglas et al. | |
| 3,992,403 A | 11/1976 | Roebke | |
| 4,169,108 A * | 9/1979 | Bailey | ........................ 564/378 |

FOREIGN PATENT DOCUMENTS
EP    0447285    9/1991

OTHER PUBLICATIONS

*French Search Report for French Application No. 04.01437*, Sep. 15, 2004.
*European Search Report for European Application No. 05290310*, Jun. 16, 2005.
*International Search Report for International Application No. PCT/FR2005/000325*, Jun. 16, 2005.
Depreux, et al., *J. Med. Chem.*, 1994, 37, 3231-3239.

* cited by examiner

*Primary Examiner* — James O Wilson
*Assistant Examiner* — Ebenezer O Sackey
(74) *Attorney, Agent, or Firm* — Hueschen and Sage

(57) ABSTRACT

A process for the industrial synthesis of the compound of formula (I)

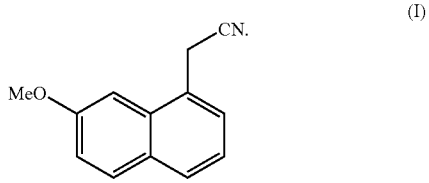

Application in the synthesis of agomelatine.

1 Claim, No Drawings

PROCESS FOR THE SYNTHESIS OF (7-METHOXY-1-NAPHTHYL) ACETONITRILE AND ITS APPLICATION IN THE SYNTHESIS OF AGOMELATINE

FIELD OF THE INVENTION

The present invention relates to a process for the industrial synthesis of (7-methoxy-1-naphthyl)acetonitrile and to its application in the industrial production of agomelatine, or N-[2-(7-methoxy-1-naphthyl)ethyl]acetamide.

More specifically, the present invention relates to a process for the industrial synthesis of the compound of formula (I):

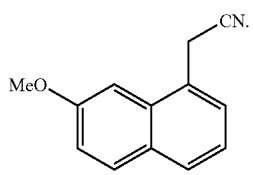

The compound of formula (I) obtained according to the process of the invention is useful in the synthesis of agomelatine, or N-[2-(7-methoxy-1-naphthyl)ethyl]acetamide, of formula (II):

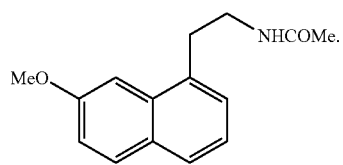

BACKGROUND OF THE INVENTION

Agomelatine, or N-[2-(7-methoxy-1-naphthyl)ethyl]acetamide, has valuable pharmacological properties.

Indeed it has the double feature of being, on the one hand, an agonist of melatoninergic system receptors and, on the other hand, an antagonist of the 5-HT$_{2C}$ receptor. Those properties confer activity in the central nervous system and, more especially, in the treatment of severe depression, seasonal affective disorders, sleep disorders, cardiovascular pathologies, pathologies of the digestive system, insomnia and fatigue resulting from jetlag, appetite disorders and obesity.

DESCRIPTION OF THE PRIOR ART

Agomelatine, its preparation and its therapeutic use have been described in European Patent Specification EP 0 447 285.

In view of the pharmaceutical value of this compound, it has been important to be able to obtain it by an effective industrial synthesis process that is readily transposable to an industrial scale and that results in agomelatine in a good yield and with excellent purity.

Patent Specification EP 0 447 285 describes the preparation of agomelatine in eight steps, starting from 7-methoxy-1-tetralone, giving an average yield of less than 30%.

That process involves the action of ethyl bromoacetate, followed by aromatisation and saponification to yield the corresponding acid, which is then converted to acetamide and subsequently dehydrated to yield (7-methoxy-1-naphthyl)acetonitrile, this being followed by reduction, and then condensation of the acetyl chloride.

In particular, the preparation of (7-methoxy-1-naphthyl)acetonitrile involves six reaction steps and, transposed to an industrial scale, has quickly demonstrated the difficulties of carrying out the process, these being caused principally by problems of reproducibility of the first step, which constitutes the action of ethyl bromoacetate on 7-methoxy-1-tetralone according to the Réformatsky reaction resulting in ethyl (7-methoxy-3,4-dihydro-1(2H)-naphthalenylidene)ethanoate.

Moreover, the subsequent step of aromatisation of ethyl (7-methoxy-3,4-dihydro-1(2H)-naphthalenylidene)ethanoate has often been incomplete and resulted, after saponification, in a mixture of products that is difficult to purify.

The literature describes obtaining (7-methoxy-1-naphthyl)acetonitrile in three steps starting from 7-methoxy-1-tetralone, by the action of LiCH$_2$CN followed by dehydrogenation with DDQ (2,3-dichloro-5,6-dicyano-1,4-benzoquinone) and finally dehydration in acid medium (Synthetic Communication, 2001, 31(4), 621-629). The total yield is mediocre (76%), however, and in particular the DDQ used in the dehydrogenation reaction and the benzene reflux necessary in the third step do not comply with industrial requirements in terms of cost and the environment.

The Applicant has now developed a new industrial synthesis process that results, in a reproducible manner and without the need for laborious purification, in agomelatine of a purity compatible with its use as a pharmaceutical active ingredient.

An alternative to the difficulties encountered with the process described in Patent Specification EP 0 447 285 has been to consider aromatisation of a substrate that does not require drastic conditions, and that allows reagents compatible with industrial requirements in terms of cost and the environment to be used.

DETAILED DESCRIPTION OF THE INVENTION

The Applicant has now developed a new industrial synthesis process that allows (7-methoxy-1-naphthyl)acetonitrile to be obtained in a reproducible manner and without the need for laborious purification.

More specifically, the present invention relates to a process for the industrial synthesis of the compound of formula (I):

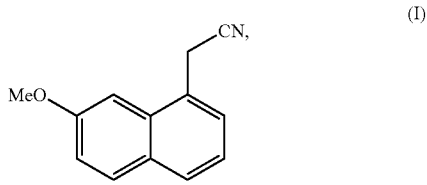

which is characterised in that (7-methoxy-3,4-dihydro-1-naphthalenyl)acetonitrile of formula (III):

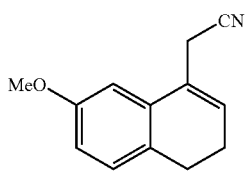

is reacted with a hydrogenation catalyst in the presence of an allyl compound, to yield the compound of formula (I) after filtration and removal of the solvent by evaporation, which compound of formula (I) is isolated in the form of a solid after recrystallisation, wherein:

"allyl compound" is understood as any molecule containing from 3 to 10 carbon atoms, which may contains in addition 1 to 5 oxygen atoms, and containing at least one —CH$_2$—CH=CH$_2$ group.

Preferably, the reaction is carried out with reflux of toluene or xylene and, more especially, with reflux of toluene.

The catalyst preferably used is a catalyst either in oxide form or supported as for example palladium, platinum, nickel, Al$_2$O$_3$ and, more especially, palladium. Advantageously, 1 to 20% palladium-on-carbon will be used, and more particularly 5% or 10% palladium-on-carbon. Preferably, palladium-on-carbon will be used in amounts ranging from 1 to 10% by weight of catalyst in relation to the weight of substrate, and more especially 5%. The hydrogen acceptor preferably used is an allyl compound and, more especially, an allyl acrylate or an allyl glycidyl ether. The preferred allyl acrylate of the process according to the invention is allyl methacrylate.

This process is of particular interest for the following reasons:

the use of a hydrogenation catalyst in the presence of an allyl compound is entirely compatible with industrial requirements in terms of cost and the environment, unlike the quinones currently used, furthermore, it allows the compound of formula (I), exclusively, in particular free from the corresponding reduction product of formula (IV):

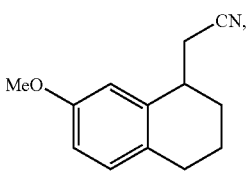

to be obtained on an industrial scale, finally, the observed rates of conversion are high, exceeding 90%.

The compound of formula (I) so obtained is, if necessary, subjected to reduction and then to coupling with acetic anhydride to yield agomelatine.

The Examples below illustrate the invention but do not limit it in any way.

EXAMPLE 1

(7-Methoxy-1-naphthyl)acetonitrile

There are introduced into a 670 litre reactor 12.6 kg of 5% palladium-on-carbon in toluene, which is heated at reflux; then 96.1 kg of (7-methoxy-3,4-dihydro-1-naphthalenyl)-acetonitrile dissolved in toluene are added as well as 63.7 kg of allyl methacrylate. The reaction is continued at reflux and is followed by vapour phase chromatography. When all the starting substrate has disappeared, the reaction mixture is cooled to ambient temperature and then filtered. After removal of the toluene by evaporation, the resulting solid residue is recrystallised from an ethanol/water (80/20) mixture to give the title product in a yield of 91% and with a chemical purity exceeding 99%.

Melting point: 83° C.

We claim:

1. A process for the synthesis of agomelatine, N-[2-(7-methoxy-1-naphthyl)ethyl]acetamide, wherein (7-methoxy-3,4-dihydro-1-naphthalenyl)acetonitrile of formula (III):

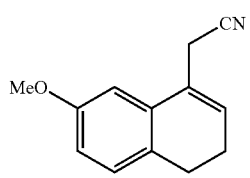

is reacted with a hydrogenation catalyst selected from palladium, platinum, nickel, and Al$_2$O$_3$ in the presence of an allyl compound, wherein "allyl" compound means any molecule containing from 3 to 10 carbon atoms, which may additionally contain 1 to 5 oxygen atoms, and containing at least one —CH$_2$—CH=CH$_2$ group, wherein the reaction is carried out in a solvent selected from xylene and toluene, to yield a compound of formula (I) after filtration and removal of solvent by evaporation:

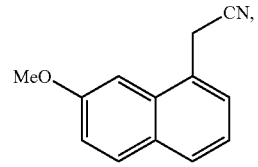

which compound of formula (I) is isolated in the form of a solid after recrystallisation, and which compound of formula (I) is subjected to reduction and then to coupling with acetic anhydride to yield agomelatine.

* * * * *